US011896333B2

(12) United States Patent
Kingsley et al.

(10) Patent No.: US 11,896,333 B2
(45) Date of Patent: Feb. 13, 2024

(54) ROBOTIC SURGICAL INSTRUMENT (71) Applicant: Covidien LP, Mansfield, MA (US)

(72) Inventors: Dylan R. Kingsley, Broomfield, CO (US); Jason G. Weihe, Longmont, CO (US); William R. Whitney, Boulder, CO (US); Russell W. Holbrook, Longmont, CO (US); Zachary S. Heiliger, Nederland, CO (US); Curtis M. Siebenaller, Frederick, CO (US); Crystal A. Adams, Westminster, CO (US); Kurt J. Anglese, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 656 days.

(21) Appl. No.: 16/997,413

(22) Filed: Aug. 19, 2020

(65) Prior Publication Data
US 2022/0054211 A1 Feb. 24, 2022

(51) Int. Cl.
*A61B 34/00* (2016.01)
*A61B 34/35* (2016.01)
*A61B 90/00* (2016.01)
*B25J 15/00* (2006.01)
*B25J 15/02* (2006.01)

(52) U.S. Cl.
CPC .............. *A61B 34/70* (2016.02); *A61B 34/35* (2016.02); *A61B 90/03* (2016.02); *B25J 15/0028* (2013.01); *B25J 15/022* (2013.01); *B25J 15/0226* (2013.01)

(58) Field of Classification Search
CPC ......... A61B 34/70; A61B 34/35; A61B 34/30; A61B 18/1445; A61B 2034/305; A61B 90/03; A61B 2017/2908; A61B 34/71; B25J 15/022; B25J 15/0028; B25J 15/0226
See application file for complete search history.

(56) References Cited

U.S. PATENT DOCUMENTS 5,752,973 A  5/1998 Kieturakis
5,792,135 A  8/1998 Madhani et al.
(Continued)

FOREIGN PATENT DOCUMENTS

WO    2017136710 A2    8/2017
WO    WO-2019036418 A1 *  2/2019  ......... A61B 18/1206
(Continued)

OTHER PUBLICATIONS

International Search Report and Written Opinion dated Nov. 24, 2021, issued in corresponding international appln. No. PCT/US2021/046459, 15 pages.
(Continued)

*Primary Examiner* — Ryan J. Severson
(74) *Attorney, Agent, or Firm* — Carter, DeLuca & Farrell LLP (57) ABSTRACT

A robotic surgical instrument includes a housing, a shaft assembly extending distally from the housing, and an end effector assembly. The shaft assembly has a proximal segment coupled to the housing, a clevis supporting the end effector assembly, and an articulating link pivotably coupled to and interconnecting the proximal segment and the clevis such that the end effector assembly is configured to articulate relative to the proximal segment via the articulating link in at least two directions.

21 Claims, 9 Drawing Sheets (56) References Cited

U.S. PATENT DOCUMENTS

| | | | |
|---|---|---|---|
| 5,848,986 A | 12/1998 | Lundquist et al. | |
| 6,394,998 B1 * | 5/2002 | Wallace | A61B 34/35 |
| | | | 901/29 |
| 6,817,974 B2 | 11/2004 | Cooper et al. | |
| 6,840,938 B1 * | 1/2005 | Morley | A61B 34/71 |
| | | | 901/29 |
| 7,799,028 B2 | 9/2010 | Schechter et al. | |
| 7,861,906 B2 | 1/2011 | Doll et al. | |
| 7,918,230 B2 | 4/2011 | Whitman et al. | |
| 8,579,176 B2 | 11/2013 | Smith et al. | |
| 9,055,961 B2 | 6/2015 | Manzo et al. | |
| 9,474,569 B2 | 10/2016 | Manzo et al. | |
| 2002/0099371 A1 | 7/2002 | Schulze et al. | |
| 2002/0177842 A1 | 11/2002 | Weiss | |
| 2003/0125734 A1 | 7/2003 | Mollenauer | |
| 2003/0208186 A1 | 11/2003 | Moreyra | |
| 2006/0022015 A1 | 2/2006 | Shelton et al. | |
| 2006/0025811 A1 | 2/2006 | Shelton | |
| 2006/0079889 A1 * | 4/2006 | Scott | A61B 18/1445 |
| | | | 606/45 |
| 2007/0233052 A1 * | 10/2007 | Brock | A61B 34/71 |
| | | | 606/1 |
| 2007/0282358 A1 | 12/2007 | Remiszewski et al. | |
| 2008/0015631 A1 | 1/2008 | Lee et al. | |
| 2010/0179540 A1 * | 7/2010 | Marczyk | A61B 18/1445 |
| | | | 606/41 |
| 2010/0274265 A1 | 10/2010 | Wingardner et al. | |
| 2010/0292691 A1 | 11/2010 | Brogna | |
| 2011/0118707 A1 * | 5/2011 | Burbank | A61B 34/37 |
| | | | 606/1 |
| 2011/0118708 A1 | 5/2011 | Burbank et al. | |
| 2011/0118709 A1 | 5/2011 | Burbank | |
| 2011/0118754 A1 | 5/2011 | Dachs, II et al. | |
| 2012/0289946 A1 * | 11/2012 | Steger | A61B 34/30 |
| | | | 606/1 |
| 2013/0123783 A1 * | 5/2013 | Marczyk | A61B 18/1445 |
| | | | 606/1 |
| 2013/0140835 A1 * | 6/2013 | Stefanchik | A61B 17/29 |
| | | | 294/106 |
| 2014/0012290 A1 * | 1/2014 | Cooper | A61B 17/29 |
| | | | 606/130 |
| 2016/0066982 A1 | 3/2016 | Marczyk et al. | |
| 2016/0256152 A1 * | 9/2016 | Kostrzewski | A61B 17/42 |
| 2017/0224367 A1 * | 8/2017 | Kapadia | A61B 34/30 |
| 2018/0206904 A1 * | 7/2018 | Felder | A61B 34/30 |
| 2019/0298466 A1 | 10/2019 | Klein et al. | |
| 2020/0237453 A1 * | 7/2020 | Anglese | A61B 90/03 |
| 2020/0237455 A1 * | 7/2020 | Anglese | A61B 34/35 |
| 2020/0405423 A1 * | 12/2020 | Schuh | A61B 17/29 |

FOREIGN PATENT DOCUMENTS

| | | | | |
|---|---|---|---|---|
| WO | 2019118337 A1 | 6/2019 | | |
| WO | WO-2019118337 A1 * | 6/2019 | | A61B 17/29 |
| WO | 2019173268 A1 | 9/2019 | | |
| WO | WO-2019173268 A1 * | 9/2019 | | A61B 34/35 |

OTHER PUBLICATIONS

International Search Report No. PCT/US2021/046459 dated Feb. 16, 2023.

* cited by examiner

ROBOTIC SURGICAL INSTRUMENT

FIELD

The present disclosure relates to surgical instruments and, more specifically, to articulating surgical instruments for use in robotic surgical systems.

BACKGROUND

Robotic surgical systems are increasingly utilized in various surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The surgical instruments or portions thereof may be configured as single-use instruments or portions that are discarded after use, or may be configured as reusable instruments or portions that are cleaned and sterilized between uses. Regardless of the configurations of the surgical instruments, the console and robotic arm are capital equipment configured for long-term, repeated use. The console and robotic arm may be protected by a sterile barrier during use and/or wiped clean after use to ensure cleanliness for subsequent uses.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. To the extent consistent, any of the aspects described herein may be used in conjunction with any or all of the other aspects described herein.

Provided in accordance with aspects of the present disclosure is a robotic surgical instrument including a housing, a shaft assembly extending distally from the housing, and an end effector assembly. The shaft assembly includes a proximal segment coupled to the housing, a clevis defining a slot in a proximal end thereof, a distal segment fixed to the clevis and having a nub keyed to the slot of the clevis, and an articulating link pivotably coupled to and interconnecting the proximal segment and the distal segment. The end effector assembly is coupled to the clevis and extends distally therefrom. The end effector assembly is configured to articulate relative to the proximal segment via the articulating link.

In aspects, the distal segment may define a depression therein, and the articulating link may have a pivot flag pivotably received in the depression.

In aspects, the distal segment may include a body portion received in the proximal end of the clevis, and a pair of opposed, spaced-apart pivot flags extending proximally from the body portion. Each of the pivot flags of the distal segment may be pivotably coupled to the articulating link.

In aspects, the articulating link may have a pair of opposed, spaced-apart pivot flags, and the distal segment may include a pair of opposed, spaced-apart pivot flags pivotably coupled to the respective pivot flags of the articulating link.

In aspects, the distal segment may define first and second depressions therein, and the pivot flags of the articulating link may be pivotably received in the respective first and second depressions.

In aspects, the first depression and the nub of the distal segment may be longitudinally aligned with one another.

In aspects, the clevis may include an elongated outer body defining a longitudinally-extending slot therein. The first jaw member may have a proximal flange received in the slot such that the elongated outer body prevents lateral movement of the first jaw member.

In aspects, the clevis may define a longitudinally-extending central channel therethrough configured for passage of a plurality of actuation components.

In aspects, the plurality of actuation components may extend distally from the housing and through the shaft assembly to operably couple to at least one of: the end effector assembly, the clevis, or the distal segment to enable selective actuation of the end effector assembly.

In aspects, actuating the end effector assembly may include at least one of: articulating the end effector assembly; manipulating the end effector assembly; advancing a component through the end effector assembly; or energizing the end effector assembly.

In aspects, the clevis may have a first wall projecting into the central channel. The first wall may define a longitudinally-extending first passageway configured for slidable receipt of at least one of a knife rod or a knife blade.

In aspects, the first passageway may have an arcuate section configured for slidable receipt of the knife rod, and a planar section configured for slidable receipt of the knife blade.

In aspects, the clevis may further include a second inner wall projecting into the central channel. The second inner wall may define a pair of longitudinally-extending second and third passageways configured for receipt of a pair of first and second electric wires.

In aspects, the second inner wall may have a first opening extending from the central channel into the second passageway to allow for lateral passage of the first wire into the second passageway. The second inner wall may have a second opening extending from the central channel into the third passageway to allow for lateral passage of the second wire into the third passageway.

In aspects, the clevis may include an elongated outer body, and the first and second inner walls may extend inwardly from the elongated outer body.

In aspects, the elongated outer body and the first and second inner walls may be monolithically formed.

In aspects, the elongated outer body may define a planar inner surface that overlaps the first inner wall to define a longitudinally-extending fourth passageway configured to guide a cam bar to the end effector assembly.

In accordance with another aspect of the disclosure, a robotic surgical instrument is provided that includes a housing, a shaft assembly extending distally from the housing, and an end effector assembly. The shaft assembly includes a proximal segment coupled to the housing, a clevis, and an articulating link pivotably coupled to an interconnecting the proximal segment and clevis. The clevis defines a longitudinally-extending central channel therethrough configured for passage of a plurality of actuation components. The end effector assembly is coupled to the clevis and extends distally therefrom. The end effector assembly is configured to articulate relative to the proximal segment via the articulating link. The clevis has a first wall projecting into the central channel and defines a longitudinally-extending first passageway configured for slidable receipt of at least one of a knife rod or a knife blade.

In aspects, the clevis may include an elongated outer body that defines a longitudinally-extending slot therein. The first jaw member may have a proximal flange received in the slot such that the elongated outer body prevents lateral movement of the first jaw member.

In aspects, the clevis may further include a second inner wall projecting into the central channel and defines a pair of longitudinally-extending second and third passageways configured for receipt of a pair of first and second electric wires.

In aspects, the plurality of actuation components may extend distally from the housing and through the shaft assembly to operably couple to at least one of the end effector assembly or the clevis to enable selective actuation of the end effector assembly.

In aspects, the shaft assembly may further include a distal segment fixed to the clevis and articulatable with the clevis relative to the proximal segment.

In aspects, the distal segment may have a nub keyed to a slot defined in the clevis.

In accordance with yet another aspect of the disclosure, a shaft assembly configured for attachment to a robotic arm is provided and includes a proximal segment, a clevis, a distal segment fixed to the clevis, and an articulating link pivotably coupled to and interconnecting the proximal segment and the distal segment. The clevis includes an elongated outer body and first and second inner walls projecting from the elongated outer body into the central channel. The elongated outer body defines a longitudinally-extending central channel therethrough configured for passage of a plurality of actuation components. The first wall defines a longitudinally-extending first passageway configured for slidable receipt of at least one of a knife rod or a knife blade. The second inner wall defines a pair of longitudinally-extending second and third passageways configured for receipt of a pair of first and second electric wires. The distal segment has a nub keyed to a slot defined in the elongated outer body of the clevis.

BRIEF DESCRIPTION OF THE DRAWINGS

Various aspects and features of the present disclosure are described hereinbelow with reference to the drawings wherein.

DETAILED DESCRIPTION

Figure 1:
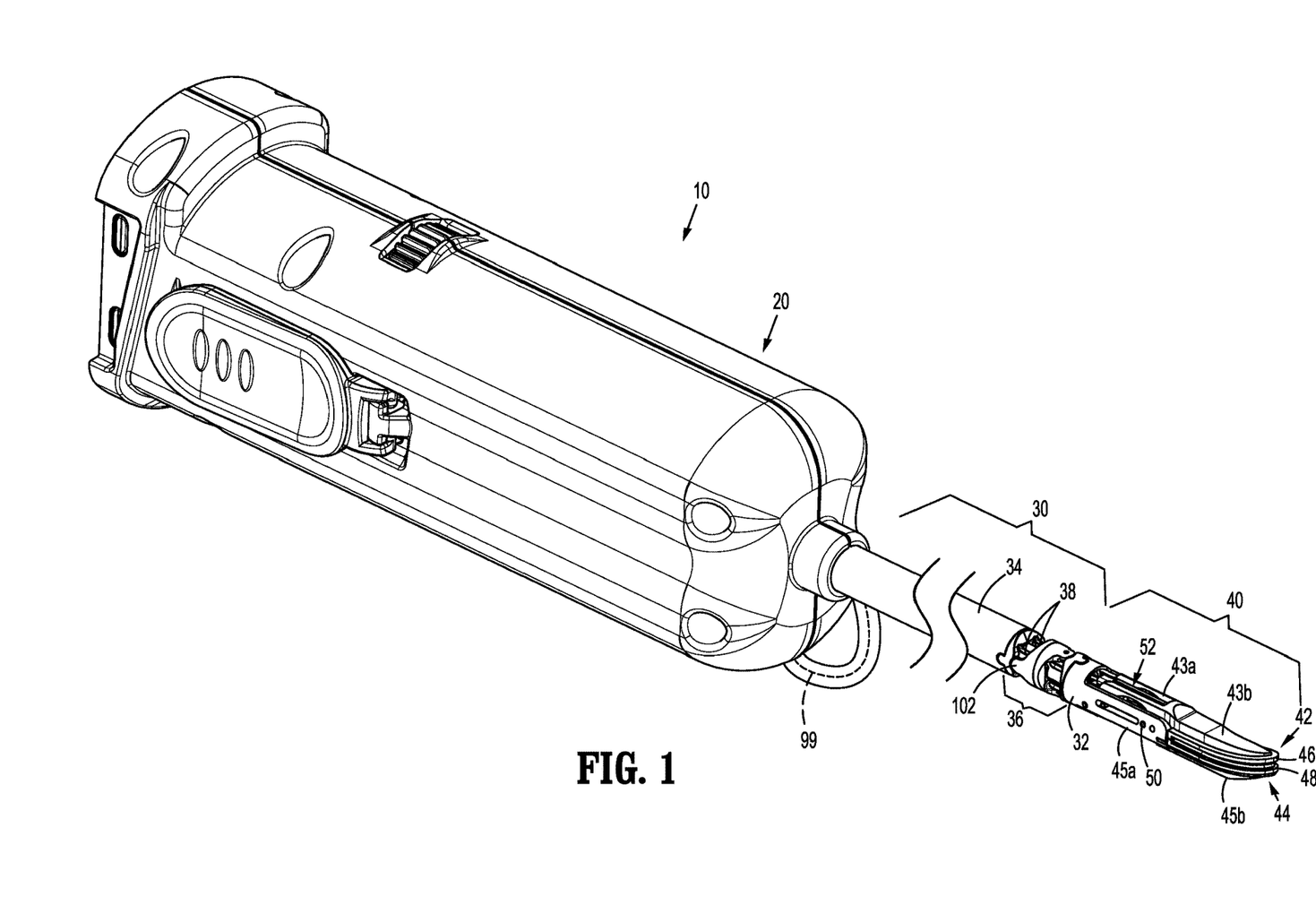
FIG. 1 is a perspective view of a surgical instrument provided in accordance with the present disclosure configured for mounting on a robotic arm of a robotic surgical system.
Figure 2:
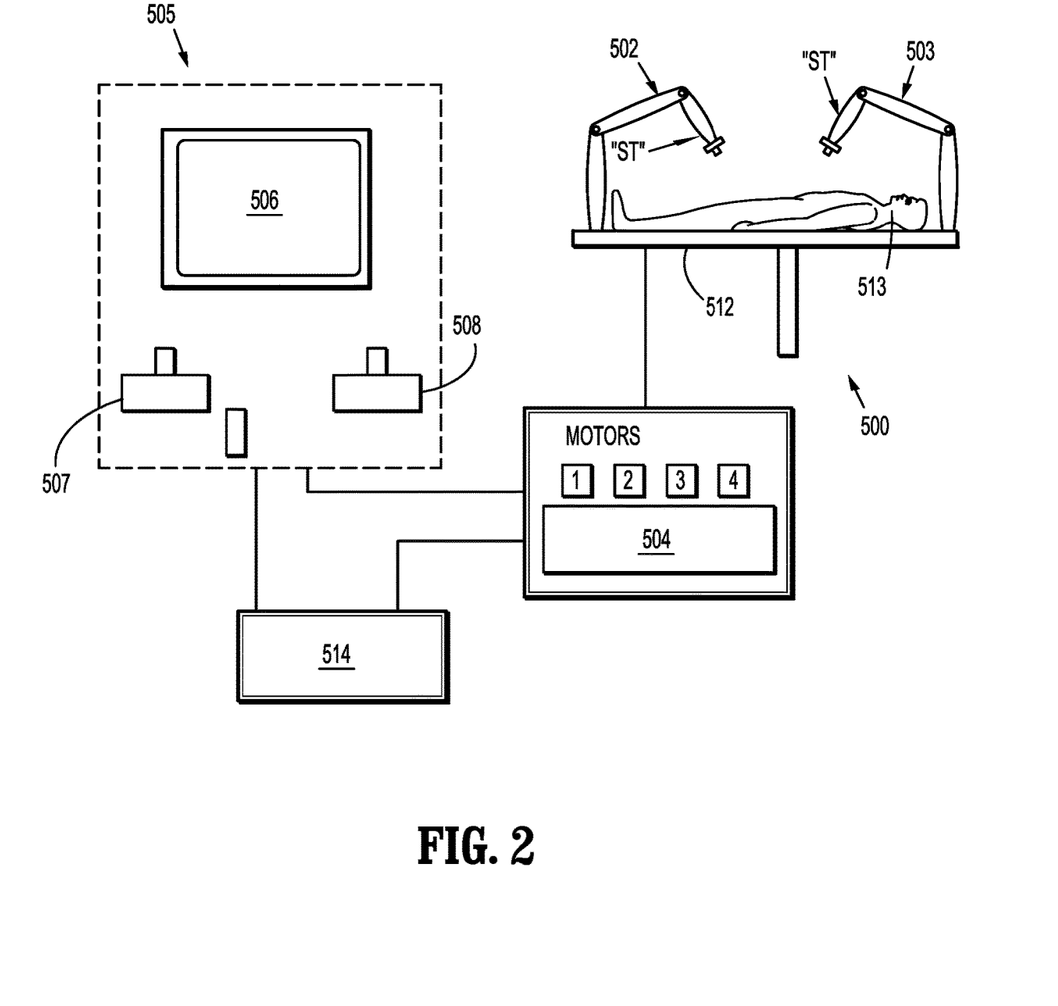
FIG. 2 is a schematic illustration of an exemplary robotic surgical system configured to releasably receive the surgical instrument of FIG. 1.

Referring to FIG. 1, a surgical instrument 10 provided in accordance with the present disclosure generally includes a housing 20, a shaft assembly 30 extending distally from housing 20, an end effector assembly 40 extending distally from shaft assembly 30, and an actuation assembly (not explicitly shown) disposed within housing 20 and operably associated with shaft assembly 30 and end effector assembly 40. Housing 20 of instrument 10 releasably engages with a robotic arm of a surgical system, e.g., robotic surgical system 500 (FIG. 2). Instrument 10 is detailed herein as an articulating electrosurgical forceps configured for use with a robotic surgical system, e.g., robotic surgical system 500 (FIG. 2). However, the aspects and features of instrument 10 provided in accordance with the present disclosure, detailed below, are equally applicable for use with other suitable surgical instruments and/or in other suitable surgical systems.

Shaft assembly 30 of instrument 10 includes a distal segment 110, a proximal segment 34, a clevis 32, and an articulating section 36 disposed between the distal and proximal segments 110, 34. Articulating section 36 includes one or more articulating components, e.g., links 104, joints, etc. A plurality of articulation cables 38, e.g., four (4) articulation cables, or other suitable actuators, extends through articulating section 36. More specifically, articulation cables 38 are operably coupled to distal segment 110 of shaft assembly 30 at the distal ends thereof and extend proximally from distal segment 110 of shaft assembly 30, through articulating section 36 of shaft assembly 30 and proximal segment 34 of shaft assembly 30, and into housing 20, wherein articulation cables 38 operably couple with an articulation assembly (not explicitly shown) of the actuation assembly to enable selective articulation of distal segment 110 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft assembly 30, actuation of articulation cables 38 is affected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

Figure 9:
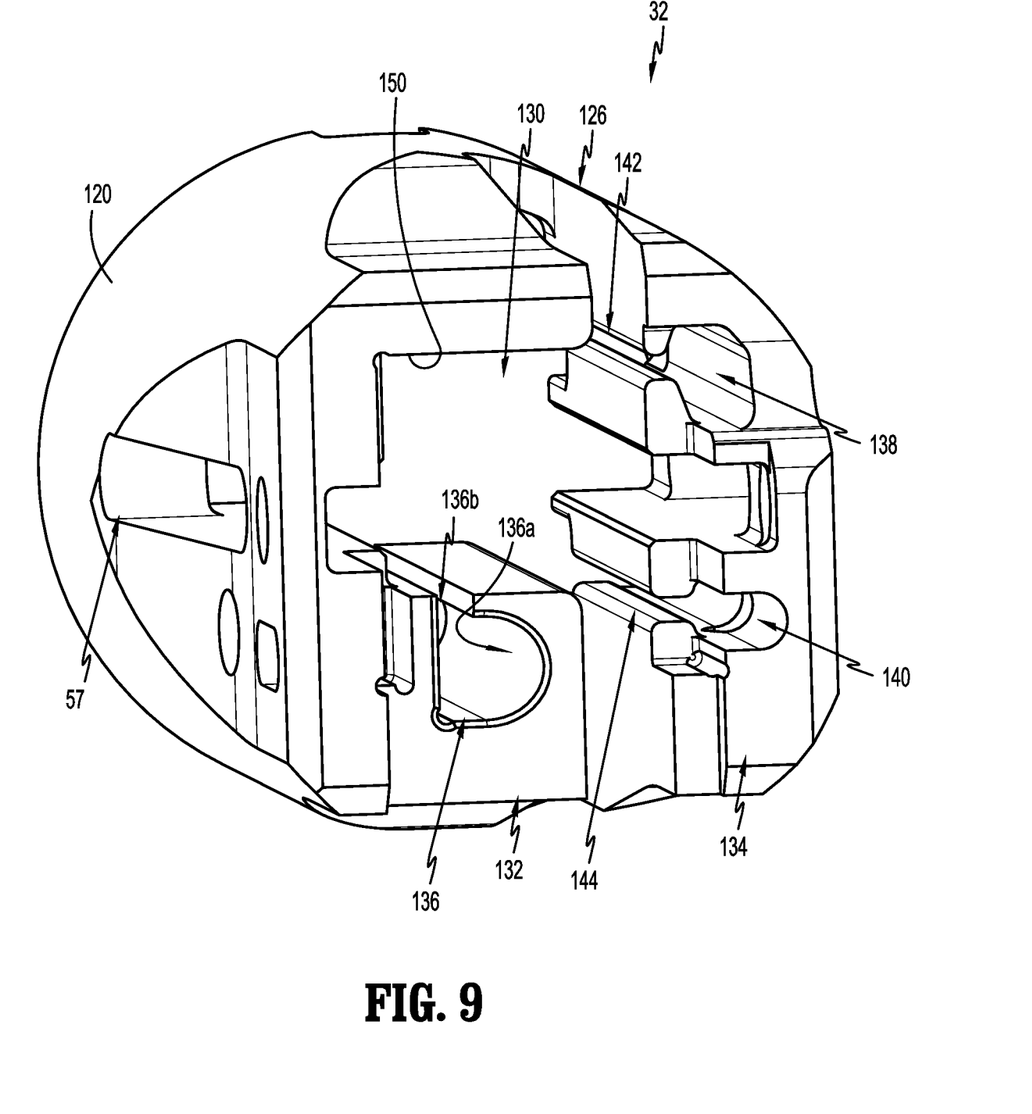
FIG. 9 is a front perspective view illustrating the internal support structures of the clevis of the shaft assembly of FIG. 3.

End effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot pin 50 and are operably coupled to one another via a cam-slot assembly 52 including a cam pin 55 slidably received within linear cam slot 57 (see FIGS. 7, 9 and 10) in clevis 32 and angled cam slot (not explicitly shown) defined within one of the proximal flange portions 43a, 45a of one of the jaw members 42, 44, respectively, to enable pivoting of jaw member 42 relative to jaw member 44 and clevis 32 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and clevis 32.

Figure 3:
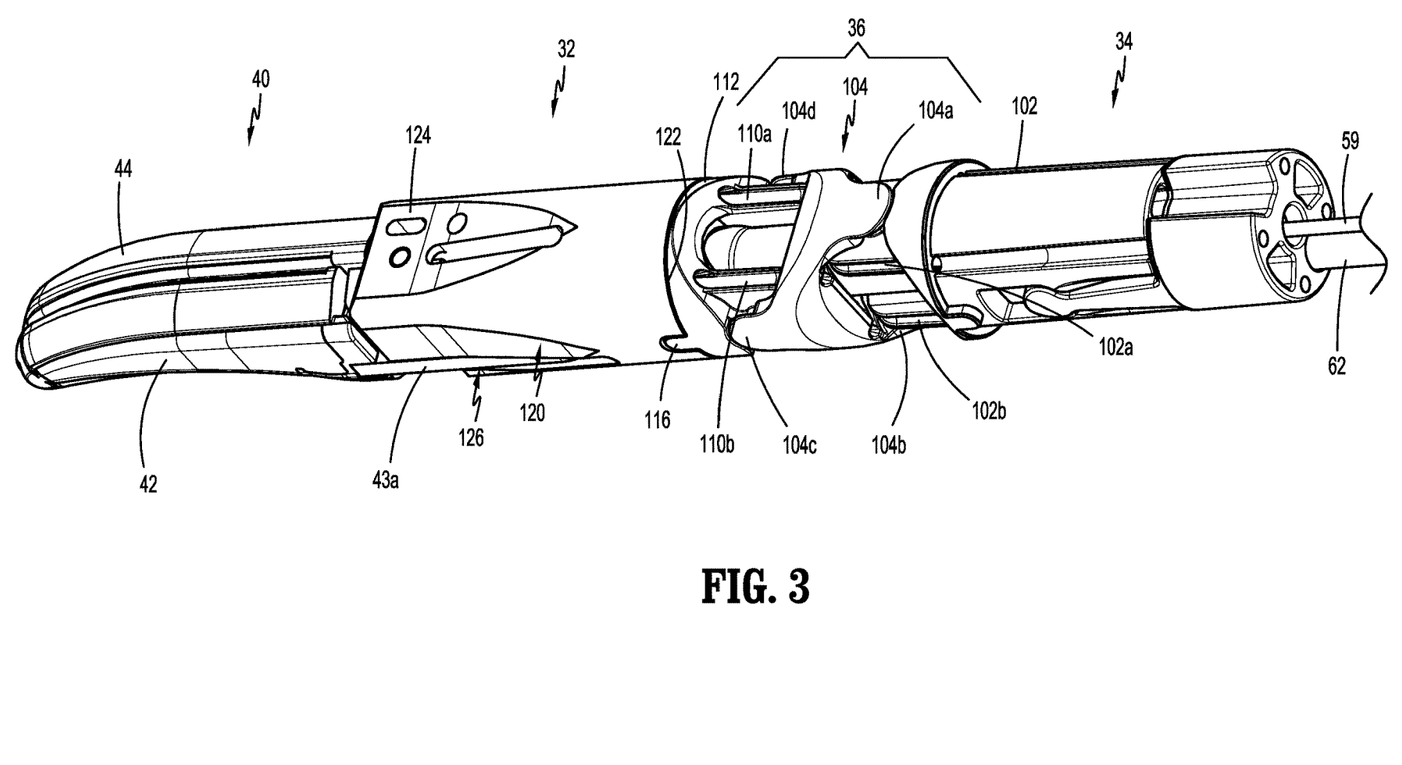
FIG. 3 is a side perspective view illustrating a portion of a shaft assembly and an end effector assembly of the surgical instrument of FIG. 1.
Figure 4:
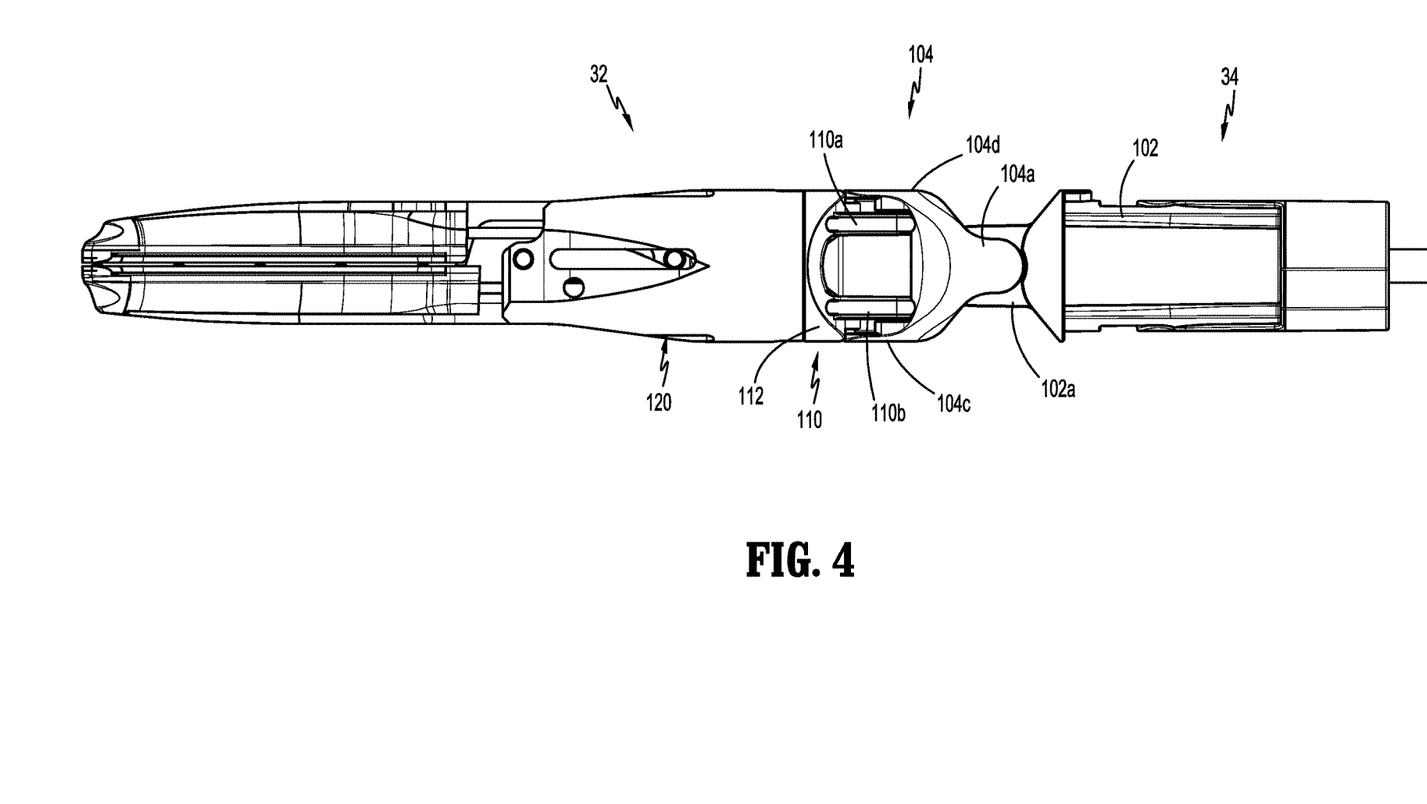
FIG. 4 is a side view of the portion of the shaft assembly and end effector assembly of FIG. 3.
Figure 5:
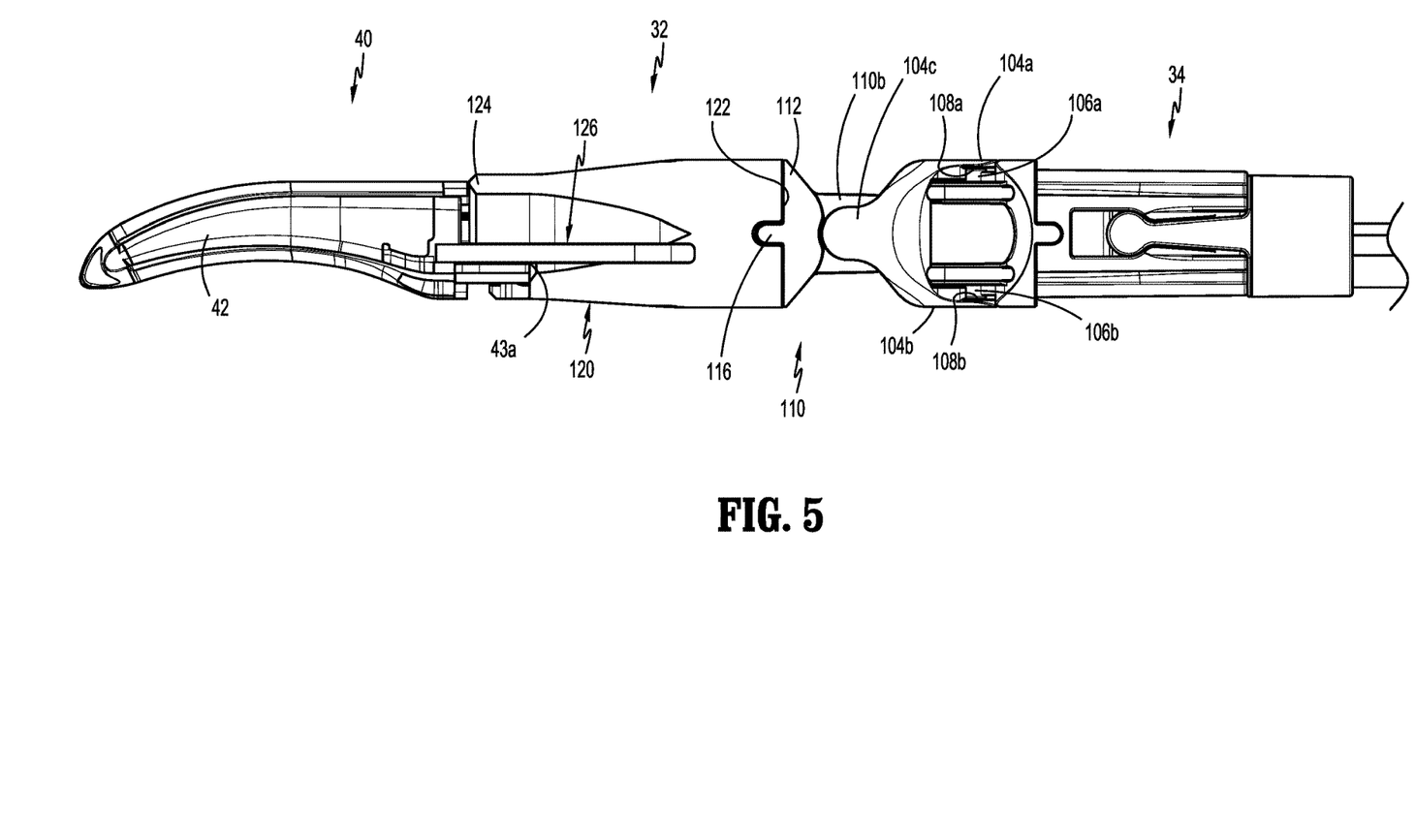
FIG. 5 is another side view of the portion of the shaft assembly and end effector assembly of FIG. 3.
Figure 6:
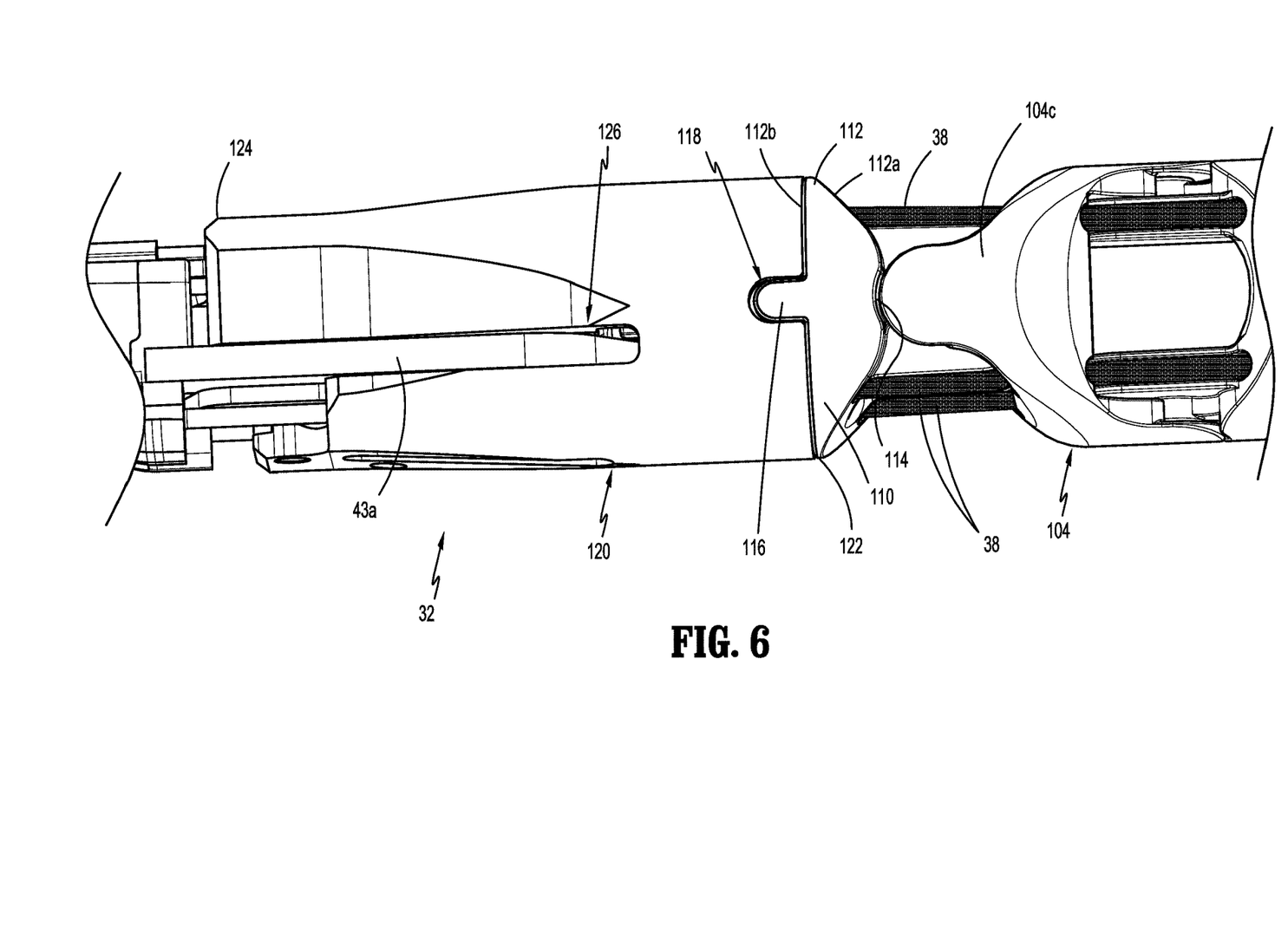
FIG. 6 is an enlarged top view of components of the shaft assembly including an articulating link, a clevis, and a distal segment.
Figure 8:
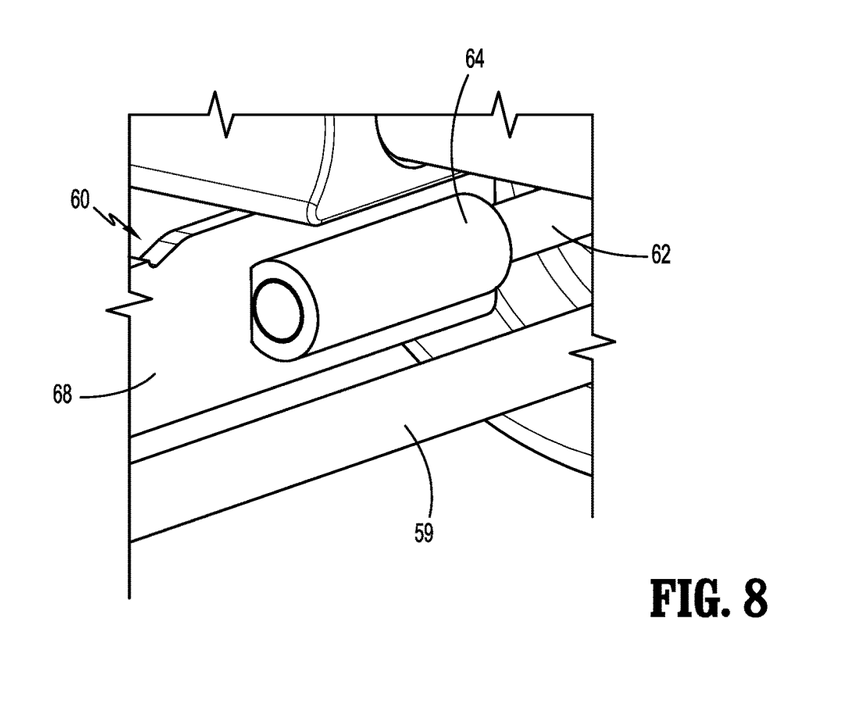
FIG. 8 is an enlarged perspective view illustrating a knife assembly of the surgical instrument of FIG. 1.
Figure 10:
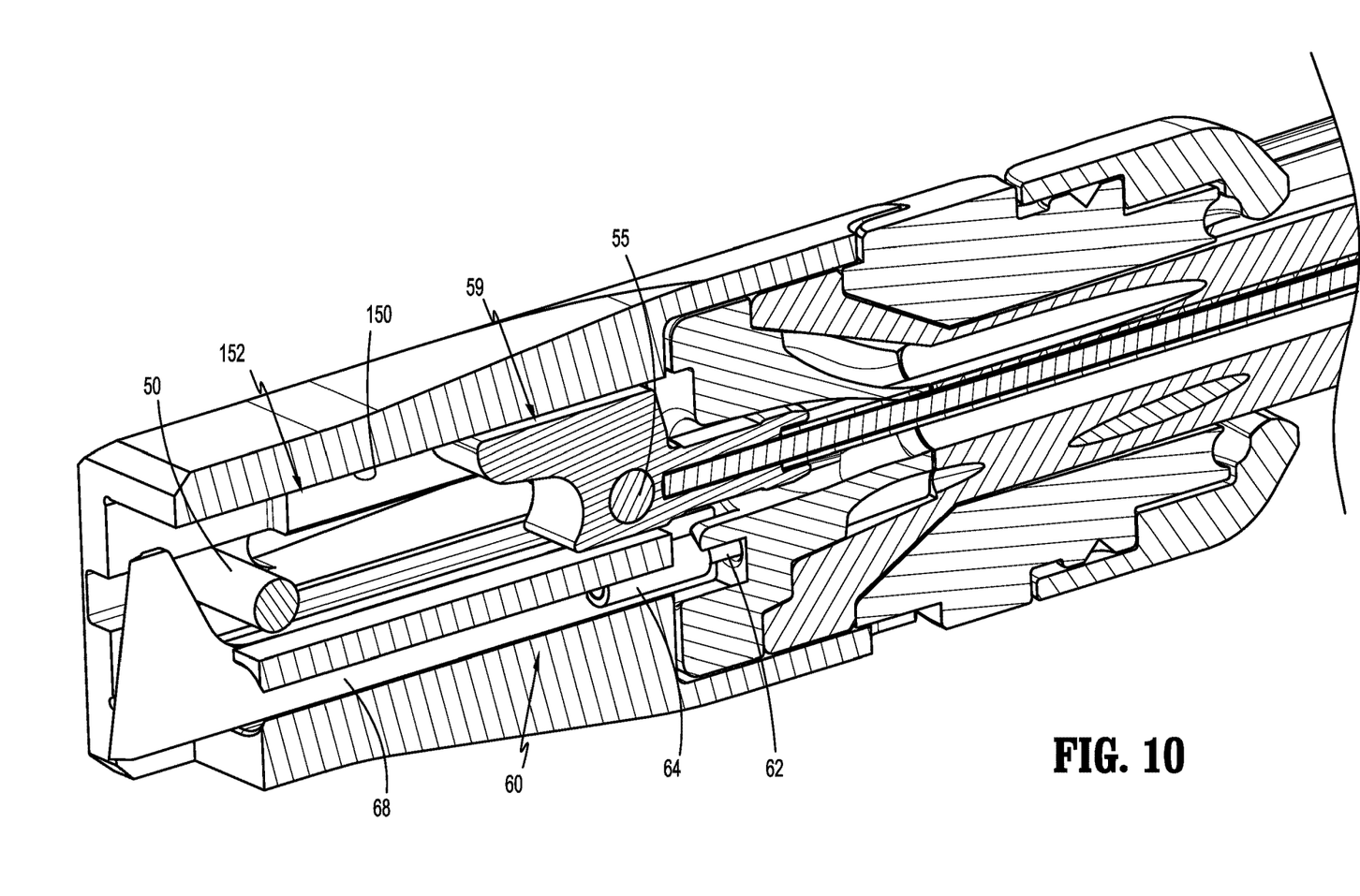
FIG. 10 is a longitudinal cross-sectional view of a distal end portion of the shaft assembly of FIG. 3 illustrating a cam bar for opening and closing the end effector assembly.

In some configurations, longitudinally-extending knife channels (not shown) are defined through tissue-contacting surfaces 46, 48, respectively, of jaw members 42, 44. In such configurations, as shown in FIGS. 3, 8 and 10, a knife assembly 60 is provided that includes a proximal knife drive tube 62, a distal knife rod 64, and a knife blade 68. The connector components 62, 64, and 68 of knife assembly 60 extend from housing 20 through shaft assembly 30 to end effector assembly 40. Knife blade 68 is disposed within end effector assembly 40 between jaw members 42, 44 and is provided to enable cutting of tissue grasped between tissue-contacting surfaces 46, 48 of jaw members 42, 44, respectively. Proximal knife tube 62 is operably coupled to a knife drive assembly (not explicitly shown) of the actuation assembly of the housing 20 to enable selective actuation thereof to, in turn, reciprocate the knife blade 68 between jaw members 42, 44 to cut tissue grasped between tissue-contacting surfaces 46, 48.

A drive rod, such as, for example, a cam bar 59 (FIGS. 3 and 10) is operably coupled to cam-slot assembly 52 of end effector assembly 40. In particular, cam bar 59 has the cam pin 55 fixed to a distal end portion thereof and the cam pin 55 is received in the cam slot of proximal flange portion 43a of jaw member 42, such that longitudinal actuation of cam bar 59 translates cam pin 55 to pivot jaw member 42 relative to jaw member 44 between the spaced-apart and approximated positions. More specifically, urging cam bar 59 proximally pivots jaw member 42 relative to jaw member 44 towards the approximated position while urging cam bar 59 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of cam bar 59 are also contemplated. Cam bar 59 extends proximally from end effector assembly 40 through shaft assembly 30 and into housing 20 wherein cam bar 59 is operably coupled with a jaw drive assembly (not explicitly shown) of the actuation assembly of housing 20 to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines a conductive pathway (not shown) through housing 20 and shaft assembly 30 to end effector assembly 40 that may include electric lead wires 99 (FIG. 1), contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48.

For further details about housing 20 and the actuation mechanism thereof (e.g., including the articulation assembly, the knife drive assembly, and the jaw drive assembly), reference may be made to U.S. patent application Ser. No. 16/915,287, filed on Jun. 29, 2020, the entire contents of which are incorporated by reference herein.

Turning to FIG. 2, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Turning to FIGS. 3-6, in conjunction with FIG. 1, as noted above, shaft assembly 30 extends distally from housing 20 and includes distal segment 110, proximal segment 34, and articulating section 36. In some configurations, as also noted above, a proximal end portion of proximal segment 34 of shaft assembly 30 extends into housing 20. Articulation cables 38 (FIGS. 1 and 6), knife tube 62 (FIGS. 3 and 8), and electrically-conductive structures (e.g., lead wires 99 (FIG. 1)) extend through proximal segment 34 of shaft assembly 30 to articulating section 36, distal segment 110, or end effector assembly 40 to enable articulation of end effector assembly 40 in pitch and yaw directions and to enable operation of end effector assembly 40 to grasp, treat, and/or cut tissue. In order to provide support for these components extending through shaft assembly 30 and maintain proper position, spacing, and/or orientation of these components extending through shaft assembly 30, clevis 32 is provided with various internal structures, as will be described below.

Proximal segment 34 has a distal end portion 102 having a pair of distally-extending and spaced-apart arms or pivot flags 102a, 102b pivotably coupled to an articulating link 104 of articulating section 36. More specifically, articulating link 104 includes a pair of proximally-extending and opposing first and second spaced-apart arms or pivot flags 104a, 104b disposed on and pivotably engaged with the corresponding pivot flags 102a, 102b of proximal segment 34. It is contemplated that pivot flags 102a, 102b of proximal segment 34 may have bosses 106a, 106b (FIG. 5) on outer-facing surfaces thereof that are pivotably received in corresponding apertures 108a, 108b (FIG. 5) defined in inner-facing surfaces of first and second pivot flags 104a, 104b of articulating link 104. Articulating link 104 further includes a pair of distally-extending and opposing third and fourth arms or pivot flags 104c, 104d that are offset about 90 degrees from the respective first and second pivot flags 104a, 104b. The third and fourth pivot flags 104c, 104d of articulating link 104 overlap with and pivotably engage corresponding first and second arms or pivot flags 110a, 110b of distal segment 110 of shaft assembly 30.

Distal segment 110 of shaft assembly 30 includes an annular body portion 112 non-rotationally fixed within a proximal opening defined in clevis 32. The first and second pivot flags 110a, 110b of the distal segment 110 extend proximally from annular body portion 112 thereof. It is contemplated that first and second pivot flags 110a, 110b of distal segment 110 pivotably couple to third and fourth pivot flags 104c, 104d of articulating link 104 via a pivotable receipt of bosses of pivot flags 110a, 110b of distal segment 110 in corresponding rounded apertures defined in third and fourth pivot flags 104c, 104d of articulating link 104. In this way, the articulating link 104, along with distal segment 110 and clevis 32, are configured to articulate relative to proximal segment 34 about a first pivot axis to adjust a yaw of end effector assembly 40, and about a second pivot axis, perpendicular to first pivot axis, to adjust a pitch of end effector assembly 40.

Annular body portion 112 of distal segment 110 has a proximal edge 112a defining a first and second opposing depressions 114 (only first depression is shown) having distal ends of the third and fourth pivot flags 104c, 104d of articulating link 140 pivotably received therein. The depressions 114 maintain the alignment of articulating link 104 and distal segment 110 while facilitating relative pivotal motion therebetween. The annular body portion 112 of distal segment 110 has a distal surface 112b from which a nub or finger 116 of distal segment 110 extends distally. The nub 116 of distal segment 110 is longitudinally aligned with first depression 114 of distal segment 110 and is configured for receipt in a slot 118 defined in clevis 32.

More specifically, clevis 32 includes an elongated outer body 120 having a proximal end 122 that defines the slot 118 therein. Slot 118 extends distally from proximal end 122 of elongated outer body 120. During assembly of shaft assembly 30, nub 116 of distal segment 110 is rotationally aligned with slot 118 in clevis 32, whereby annular body portion 112 of distal segment 110 is positioned into the clevis 32 and nub 116 of distal segment 110 is keyed to slot 118 of clevis 32. With nub 116 keyed to slot 118, distal segment 110 and clevis 32 are rotationally fixed relative to one another.

Elongated outer body 120 of clevis 32 has a distal end 124 to which end effector assembly 40 is coupled. Distal end 124 of elongated outer body 120 defines a slot 126 that extends proximally from distal end 124. The proximal flange portion 43a of first jaw member 42 is received in the slot 126 such that the elongated outer body 120 prevents lateral movement of the first jaw member 42. It is contemplated that elongated outer body 120 of clevis 32 defines another slot on an opposite side of distal end 124 configured for receipt of proximal flange portion 45a of second jaw member 44.

With reference to FIGS. 7-10, elongated outer body 120 of clevis 32 defines a longitudinally-extending central channel 130 therethrough configured for passage of a plurality of actuation components (e.g., articulation cables 38, knife assembly 60, electric wires 99, cam bar 59, etc.). The actuation components extend distally from the housing 20 (FIG. 1) and through the shaft assembly 30 to operably couple to the end effector assembly 40, the clevis 32, or the distal segment 110 to enable selective actuation of the end effector assembly 40. Actuating the end effector assembly 40 includes articulating the end effector assembly 40 via articulation cables 38, advancing knife blade 68 through the end effector assembly 20, closing jaw members 42, 44 via the cam bar 59, or energizing the end effector assembly 40 via electric wires 99.

To guide and/or position the various actuation components, clevis 32 has a plurality of support structures. In particular, clevis 32 has first and second walls 132, 134 projecting into the central channel 130 from elongated outer body 120. The first and second walls 132, 134 may be monolithically formed with elongated outer body 20, such as, for example, machined from a single source of material, such as, for example, various metals and/or plastics. The first wall 132 defines a longitudinally-extending first passageway 136 configured for slidable receipt of both the knife rod 64 and knife blade 68. The first passageway 136 has an arcuate section 136a configured for slidable receipt of the knife rod 64, and a planar section 136b configured for slidable receipt of the knife blade 68. It is contemplated that arcuate and planar sections 136a, 136b of first passageway 136 are contiguous with one another and extend longitudinally through clevis 32. In aspects, arcuate and planar sections 136a, 136b may be coated with a lubricious material to facilitate sliding of knife rod 64 and knife blade 68 through first passageway 136.

Second inner wall 134 of clevis 32 defines a pair of longitudinally-extending second and third passageways 138, 140 configured for receipt of respective first and second electric wires 99 (FIG. 1). The second inner wall 134 has a first side opening 142 extending from the central channel 130 into the second passageway 138, and a second side opening 144 extending from the central channel 130 into the third passageway 140. In this way, second inner wall 134 allows for the lateral passage or insertion of the first and second wires 99 into the second and third passageways 138, 140 via the first and second side openings 142, 144.

Figure 7:
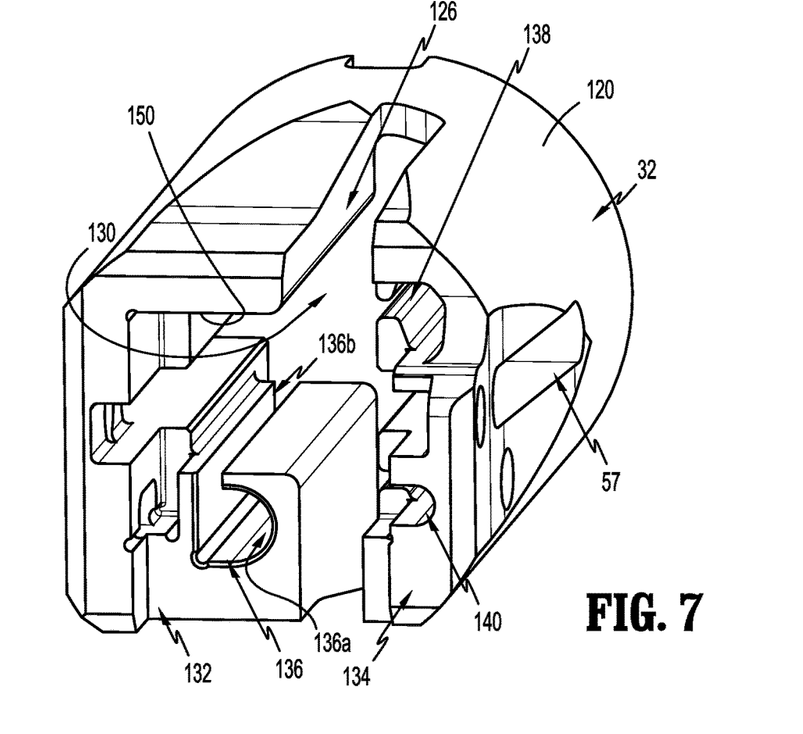
FIG. 7 is a front perspective view illustrating internal support structures of the clevis of the shaft assembly of FIG. 3.

As best shown in FIGS. 7 and 10, the elongated outer body 120 defines a planar inner-facing surface 150 that overlaps the first inner wall 132 to define a longitudinally-extending fourth passageway 152 configured to guide cam bar 59 through clevis 32. In this way, one monolithic structure, namely clevis 32, is capable of guiding/supporting all actuation components of robotic surgical instrument 10.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A robotic surgical instrument, comprising:
a housing;
a shaft assembly extending distally from the housing and including:
a proximal segment coupled to the housing;
a clevis defining a slot in a proximal end thereof;
a distal segment fixed to the clevis and having a nub keyed to the slot of the clevis; and
an articulating link pivotably coupled to and interconnecting the proximal segment and the distal segment; and
an end effector assembly coupled to the clevis and extending distally therefrom, wherein the end effector assembly is configured to articulate relative to the proximal segment via the articulating link,
wherein the distal segment defines a depression therein and the articulating link includes a pivot flag pivotably received in the depression in longitudinal alignment with the nub, and
wherein the clevis and distal segment are fixed in rotational alignment relative to one another upon operational engagement of the nub within the slot.

2. The robotic surgical instrument according to claim 1, wherein the distal segment includes:
a body portion received in the proximal end of the clevis; and
a pair of opposed, spaced-apart pivot flags extending proximally from the body portion, each of the pivot flags of the distal segment pivotably coupled to the articulating link.

3. The robotic surgical instrument according to claim 1, wherein the articulating link has a pair of opposed, spaced-apart pivot flags, and the distal segment includes a pair of opposed, spaced-apart pivot flags pivotably coupled to the respective pivot flags of the articulating link, and wherein the distal segment defines first and second depressions therein, and the pivot flags of the articulating link are pivotably received in the respective first and second depressions.

4. The robotic surgical instrument according to claim 1, wherein the clevis includes an elongated outer body defining a longitudinally-extending slot therein, the end effector having a proximal flange received in the slot such that the elongated outer body prevents lateral movement of the end effector.

5. The robotic surgical instrument according to claim 1, wherein the clevis defines a longitudinally-extending central channel therethrough configured for passage of a plurality of actuation components.

6. The robotic surgical instrument according to claim 5, wherein the plurality of actuation components extend distally from the housing and through the shaft assembly to operably couple to at least one of: the end effector assembly, the distal segment, or the clevis to enable selective actuation of the end effector assembly.

7. The robotic surgical instrument according to claim 5, wherein the clevis has a first wall projecting into the central channel, the first wall defining a longitudinally-extending first passageway configured for slidable receipt of at least one of a knife rod or a knife blade.

8. The robotic surgical instrument according to claim 7, wherein the first passageway has an arcuate section configured for slidable receipt of the knife rod, and a planar section configured for slidable receipt of the knife blade.

9. The robotic surgical instrument according to claim 7, wherein the clevis further includes a second inner wall projecting into the central channel, the second inner wall defining a pair of longitudinally-extending second and third passageways configured for receipt of a pair of first and second electric wires.

10. The robotic surgical instrument according to claim 9, wherein the second inner wall has a first opening extending from the central channel into the second passageway to allow for lateral passage of the first wire into the second passageway, and the second inner wall has a second opening extending from the central channel into the third passageway to allow for lateral passage of the second wire into the third passageway.

11. A robotic surgical instrument, comprising:
a housing;
a shaft assembly extending distally from the housing and including:
a proximal segment coupled to the housing;
a clevis defining a longitudinally-extending central channel therethrough configured for passage of a plurality of actuation components, the clevis including a slot defined in a proximal end thereof;
an articulating link pivotably coupled to and interconnecting the proximal segment and the clevis, the articulating link including a pair of spaced-apart pivot flags;
a distal segment rotationally fixed to the clevis and articulatable with the clevis relative to the proximal segment, the distal segment including a nub keyed to the slot defined in the clevis, the distal segment defining a pair of depressions configured to receive the corresponding pair of spaced-apart pivot flags of the articulating link in longitudinal alignment with the nub; and
an end effector assembly coupled to the clevis and extending distally therefrom, wherein the end effector assembly is configured to articulate relative to the proximal segment via the articulating link, wherein the clevis has a first wall projecting into the central channel, the first wall defining a longitudinally-extending first passageway configured for slidable receipt of at least one of a knife rod or a knife blade.

12. The robotic surgical instrument according to claim 11, wherein the first passageway has an arcuate section configured for slidable receipt of the knife rod, and a planar section configured for slidable receipt of the knife blade.

13. The robotic surgical instrument according to claim 11, wherein the clevis includes an elongated outer body defining a longitudinally-extending slot therein, the end effector having a proximal flange received in the slot such that the elongated outer body prevents lateral movement of the end effector.

14. The robotic surgical instrument according to claim 11, wherein the clevis further includes a second inner wall projecting into the central channel, the second inner wall defining a pair of longitudinally-extending second and third passageways configured for receipt of first and second electric wires.

15. The robotic surgical instrument according to claim 14, wherein the second inner wall has a first opening extending from the central channel into the second passageway to allow for lateral passage of the first wire into the second passageway, and the second inner wall has a second opening extending from the central channel into the third passageway to allow for lateral passage of the second wire into the third passageway.

16. The robotic surgical instrument according to claim 11, wherein the plurality of actuation components extend distally from the housing and through the shaft assembly to operably couple to at least one of the end effector assembly or the clevis to enable selective actuation of the end effector assembly.

17. The robotic surgical instrument according to claim 16, wherein actuating the end effector assembly includes at least one of: articulating the end effector assembly; manipulating the end effector assembly; advancing a component through the end effector assembly; or energizing the end effector assembly.

18. A shaft assembly configured for attachment to a robotic arm, the shaft assembly comprising:
- a proximal segment;
- a clevis including:
  - an elongated outer body defining a longitudinally-extending central channel therethrough configured for passage of a plurality of actuation components;
  - a first wall projecting from the elongated outer body into the central channel, the first wall defining a longitudinally-extending first passageway configured for slidable receipt of at least one of a knife rod or a knife blade; and
  - a second inner wall projecting from the elongated outer body into the central channel, the second inner wall defining a pair of longitudinally-extending second and third passageways configured for receipt of first and second electric wires;
- a distal segment rotationally fixed to the clevis and having a nub keyed to a slot defined in the elongated outer body of the clevis; and
- an articulating link pivotably coupled to and interconnecting the proximal segment and the distal segment, the articulating link including a pair of spaced-apart pivot flags,
- wherein the distal segment is articulatable with the clevis relative to the proximal segment, and wherein the distal segment defines a pair of depressions configured to receive the corresponding pair of spaced-apart pivot flags of the articulating link in longitudinal alignment with the nub.

19. The shaft assembly according to claim 18, wherein the first passageway has an arcuate section configured for slidable receipt of the knife rod, and a planar section configured for slidable receipt of the knife blade.

20. The shaft assembly according to claim 18, wherein the elongated outer body of the clevis defines a longitudinally-extending slot therein configured for receipt of a proximal flange of a jaw member.

21. The shaft assembly according to claim 18, wherein the second inner wall has a first opening extending from the central channel into the second passageway to allow for lateral passage of the first wire into the second passageway, and the second inner wall has a second opening extending from the central channel into the third passageway to allow for lateral passage of the second wire into the third passageway.

* * * * *